United States Patent [19]

Sams et al.

[11] Patent Number: 4,503,860
[45] Date of Patent: Mar. 12, 1985

[54] ELECTROENCEPHALOGRAPHY ELECTRODE ASSEMBLY

[75] Inventors: Marvin W. Sams, Dallas, Tex.; Samuel L. Wasson, Livonia, Mich.

[73] Assignee: Bio-Scan, Inc., Dallas, Tex.

[21] Appl. No.: 480,858

[22] Filed: Mar. 31, 1983

[51] Int. Cl.³ ............................................. A61B 5/04
[52] U.S. Cl. ................................... 128/639; 128/640
[58] Field of Search ............................ 128/639–644, 128/798, 802, 803

[56] References Cited

U.S. PATENT DOCUMENTS

| | | | |
|---|---|---|---|
| 2,872,926 | 2/1959 | Alderman | 128/640 |
| 3,547,104 | 12/1970 | Buffington | 128/640 |
| 3,607,788 | 9/1971 | Adolph et al. | 128/640 |
| 3,998,213 | 12/1976 | Price | 128/644 |
| 4,085,739 | 4/1978 | Sams | 128/2.1 B |
| 4,323,076 | 4/1982 | Sams | 128/644 |
| 4,331,153 | 5/1982 | Healy | 128/641 |
| 4,417,581 | 11/1983 | Dawson | 128/639 |

Primary Examiner—Lee S. Cohen
Attorney, Agent, or Firm—Hubbard, Thurman, Turner & Tucker

[57] ABSTRACT

Electroencephalography electrodes are attached to the surface of the scalp at predetermined points and are connected to relatively long lead wires which are anchored to the patient's skin at a short distance from the electrode itself to provide a strain relief on the lead wire and to minimize signal interference or artifacts associated with movement of the lead wire and the electrode. The arrangement provides for placing a preamplifier unit in a position on the patient's body which is more comfortable and less cumbersome than if mounted directly adjacent the electrodes themselves. The electrode and lead assembly may be provided with a thickened portion of the lead insulation to increase the surface area available for anchoring the lead by tape or other adhesive.

2 Claims, 4 Drawing Figures

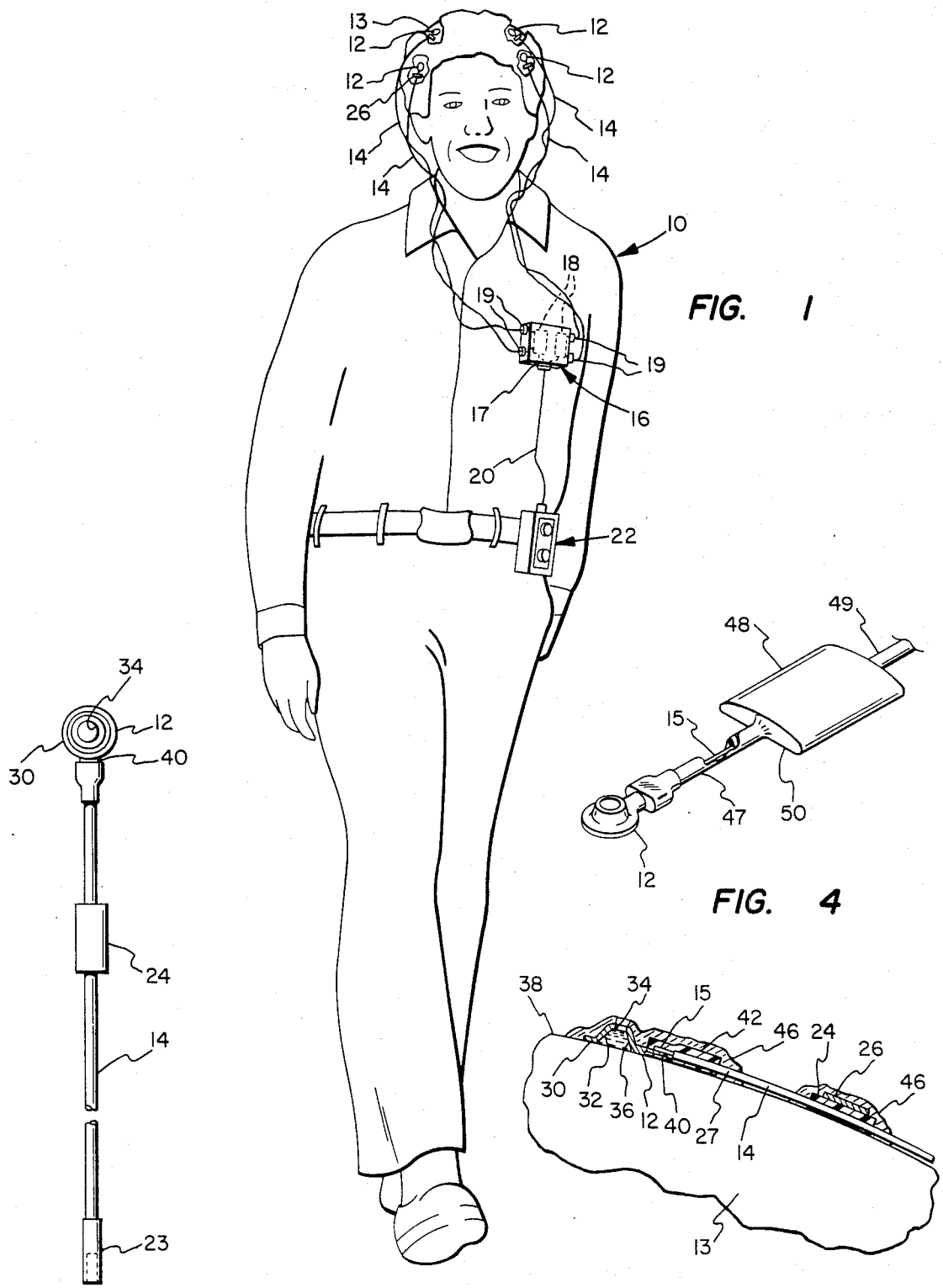

ELECTROENCEPHALOGRAPHY ELECTRODE ASSEMBLY

BACKGROUND OF THE INVENTION

1. Field of the Invention

The present invention pertains to an electrode assembly and a method of attaching one or more electrodes for measuring electrical signals generated by human organs, particularly in connection with electroencephalography.

2. Background

In the art of electroencephalography, and other techniques involving the measurement of electrical signals generated by human organs, one or more signal sensing devices or electrodes are placed in direct contact with the surface of the skin or other tissues for measuring electrical potentials generated by the organ.

In the art of electroencephalography, for example, various types of electrodes and methods of attachment to the scalp have been developed. One technique of attachment of a plurality of electrodes at various predetermined positions on the scalp utilizes a flexible cap made of a suitable fabric which must be worn by the patient during the monitoring process. My U.S. Pat. Nos. 4,085,739 and 4,323,076 disclose one preferred type of cap and an associated harness for use therewith. Although, the apparatus disclosed in the aforementioned patents is suitable for various measurement processes in clinical and hospital procedures there are many instances wherein it is desirable to measure the signals generated by the patient's brain or other organs over a relatively long period of time while permitting the patient to be ambulatory. Accordingly, the wearing of a cap or other structure for supporting the electrodes becomes uncomfortable or otherwise annoying to the patient.

However, the extremely low intensity of electrical signals generated by the brain and other organs requires techniques which minimize signal interference and which also require amplification of the signal detected by the electrodes. In this regard, it has been conventional practice to minimize the length of signal transmitting conductors or leads from the electrode to the signal amplification and/or recording equipment. In order to obtain meaningful electroencephalography devoid of extraneous signals or artifacts in ambulatory patients prior art practice in electroencephalography, has required the mounting of small preamplifier devices directly on the scalp closely adjacent to the electrodes to minimize electrode lead wire length. However, with the provision of several electrodes on the scalp, the addition of the preamplifier devices supported on the scalp closely adjacent to the electrodes is uncomfortable and interferes with normal activity of an ambulatory patient.

The mounting of preamplifier devices directly adjacent to the electrodes and the minimization of electrode lead length has been widely accepted as the only technique available to minimize so called artifacts or interfering signals generated during the recording of ambulatory electroencephalography data. Prior art arrangements of electrodes and preamplifiers have still not reduced signal interference to a degree which is desirable for providing reliable ambulatory electroencephalographs with the discovery of the present invention an improved electrode assembly and a technique for attaching a plurality of electrodes to the patient has been developed to provide more comfort without the generation of unwanted signals or interference.

SUMMARY OF THE INVENTION

The present invention provides an improved electrode assembly and method of attaching electrodes in the measurement of electroencephalography data which minimizes noise or unwanted signals generated during the measurement process. The improved electrode assembly is more comfortable to the patient since the patient is not required to wear preamplifier devices directly on the head. Moreover, the improved electrode arrangement permits the patient to be ambulatory without the use of a harness, cap or other cumbersome structure attached to the scalp.

In accordance with one aspect of the present invention it has been determined that electroencephalography signals may be detected and transmitted to a preamplifier for amplification and transmission to a further amplifier and recording unit utilizing electrodes with flexible electrical conductors or leads of substantial length between the electrode and the amplifier or preamplifier unit without incurring unwanted signal interference or artifacts. Accordingly, one or more relatively small electrodes may be attached to the scalp or at other locations on the patient's body for detecting and transmitting electrical signals of very low intensity without placing amplifier devices directly adjacent to the electrodes themselves. Such an arrangement provides for more convenience and comfort of the patient since the electrodes themselves are relatively small devices and are connected to small diameter flexible electrical leads which may be routed from the scalp to a preamplifier unit which may be worn by the patient attached to or support by the patient's clothing in a convenient, comfortable and hidden location, if desired.

In accordance with another aspect of the present invention there is provided a method for mounting and supporting one or more electrodes for measuring low intensity signals generated by the brain or other organs wherein the electrode is attached to the surface of the skin by an adhesive, and a flexible conductor or lead wire is anchored to the skin at a point a short distance from the electrode itself to stabilize the electrode in the vicinity of the measuring point and to relieve any strain on the lead at its point of connection to the electrode proper. The flexible conductor or lead is preferably a single conductor or stranded metal wire having an insulation cover provided with an anchoring sleeve secured to the insulation at a point closely adjacent to the terminal connection between the lead wire and the electrode proper. The anchoring sleeve is provided for anchoring the lead at the preferred point by suitable means such as tape and/or adhesive.

The overall length of the electrode lead may be that which is necessary to connect the lead to an amplifier or preamplifier circuit mounted on the patient's body at a point remote from the location of the electrodes themselves and for the convenience and comfort of the patient. With the arrangement of supporting the electrode and its lead as described electroencephalographic signals and other low intensity signals generated by various body organs and structures may be recorded without interference from movement of the patient's skin or muscles in the vicinity of the electrode. Accordingly, clear unadulterated signals may be amplified and recorded by conventional amplification and recording equipment used for electroencephalography and similar medical measuring and diagnostic systems.

In accordance with another aspect of the present invention there is provided an improved electrode and lead assembly for use in practicing the method of the present invention wherein a small signal sensing and conducting electrode is connected to a lead wire of substantial length and which is provided with anchoring means closely adjacent to the electrode proper for anchoring the lead and relieving strain on the electrode which might result in the generation of unwanted signals during a measuring and recording process.

Those skilled in the art will further appreciate the advantages and salient features of the method and apparatus of the invention upon reading the detailed description which follows in conjunction with the drawings.

BRIEF DESCRIPTION OF THE DRAWINGS

FIG. 1 is a front elevation of a patient wearing the improved arrangement of electroencephalography apparatus in accordance with the present invention;

FIG. 2 is a plan view of the electrode and lead assembly of the present invention;

FIG. 3 is a detail side view, in section, of an electrode attached to a patient's skin in accordance with the method and apparatus of the present invention; and FIG. 4 is a detail perspective view of an alternate embodiment of an electrode assembly.

DESCRIPTION OF THE PREFERRED EMBODIMENTS

In the description which follows, like parts are marked throughout the specification and drawings with the same reference numerals, respectively. The drawings are not necessarily to scale and certain features may be exaggerated in scale or shown in schematic form in the interest of clarity and conciseness.

Referring to FIG. 1 there is illustrated an improved arrangement for recording electroencephalography data. Although the present invention is particularly adapted for use in electroencephalography, those skilled in the art will recognize that the improvements may be used in conjunction with recording signals generated by other organs and portions of a patient's body wherein relatively low strength signals must be transmitted without interference to amplification and recording equipment. In FIG. 1, there is illustrated a patient comprising a human being 10 wherein a plurality of electroencephalographic electrodes 12 have been attached to the patient's scalp 13 in a predetermined arrangement and in accordance with the present invention. Each of the electrodes 12 is connected to an elongated flexible insulated conductor or lead 14 leading from the patient's head to a preamplifier unit, generally designated by the numeral 16. In accordance with a particularly advantageous aspect of the present invention the preamplifier unit 16 may comprise a small housing 17 having suitable preamplification circuitry 18 disposed therein and adapted to be connected to the respective leads 14 by suitable connectors 19 mounted on the housing. The amplifier circuits 18 are also adapted to generate amplified signals which may be transmitted through suitable conductor means 20 to a signal amplification and recording unit, generally designated by the numeral 22. The recording unit 22 is preferably of a type which is adapted to generate output signals related to the signals received by the electrodes 12 and to record said signals on a tape cassette or the like for subsequent analysis. The recording unit 22 may be, for example, a model 4-24 manufactured by Oxford Medilog, Inc., Clearwater, Fla. The exemplary recording unit 22 is relatively compact and easily wearable by the patient attached to a belt or placed in a jacket or vest pocket or other suitable location. Moreover, the preamplifier unit 16 is also particularly compact and may be worn by the patient in a shirt pocket or otherwise secured on the patient's clothing or attached to the patient's body in an inconspicuous and comfortable location. The preamplifier unit 16 may be enclosed in a rectangular box type housing approximately 2.5 inches square by 0.25 inches thick.

Referring now to FIG. 2, an electrode assembly including the electrode 12 and the insulated lead 14 also includes a suitable connector element 23 in electrical conductive relationship with the lead and attached to the end opposite the electrode. The connector 23 is adapted to be coupled to one of the connectors 19 on the amplifier unit 16. The lead 14 also includes suitable means for anchoring the lead at a point spaced a short distance from the terminal portion of the electrode 12, which means may comprise a short section of heat shrinkable plastic tubing 24 positioned over the insulation for the lead 14 and shrunk into gripping engagement therewith. The short section of anchoring tubing 24 is of sufficient diameter to provide an enlarged surface area for anchoring the lead at a distance of approximately one inch from the electrode itself whereby the lead may be anchored to the patient's skin by suitable means preferably comprising an adhesive such as collodion. Alternatively, or in addition to the collodion, a small piece of adhesive tape 26 may be used as will be described further herein. In accordance with the present invention the length of the lead 14 between the electrode 12 and the connector 23 may be considerably greater than heretofore appreciated by prior art practice as regards ambulatory patients. In fact, with the superior anchoring method of the present invention, the lead 14 may be of sufficient length whereby the preamplifier unit 16 may be worn virtually anywhere on the patient's body which would be considered comfortable and/or convenient.

Referring now to FIG. 3 there is illustrated a partial detail view, in section, of the electrode 12 and the portion of the lead 14 including the anchoring sleeve 24. The electrode 12 is illustrated as a small disk type electrode having a generally cylindrical flange portion 30 and an integral conical central section 32 with a central aperture 34 formed therein. The shape of the electrode 12 forms a somewhat frusto-conical shaped cavity 36 when the electrode is placed in contact with the surface of the patient's skin, generally designated by the numeral 38. The electrode 12 has a laterally projecting terminal portion 40 which is preferably soldered to the conductor wire 15 of the lead 14. An insulating sleeve 42 is preferably secured over the lead 14 including a portion of its insulation cover 27 and the conductor wire 15 at the junction of the conductor wire with the terminal 40 as illustrated in FIG. 3. The electrode 12 illustrated and described herein is exemplary and other specific electrode configurations may be used in conjunction with the method of the present invention although the particular electrode shown and described is relatively compact and may, for example, be less than 0.4 inches in diameter and approximately 0.12 inches in overall height from the contact surface 31 formed by the flange 30 to the opposed surface delimiting the opening 34.

Referring to FIG. 4, an alternate embodiment of an electrode assembly is illustrated including an electrode 12 connected to an insulated lead 47 including a conductor 15 which is connected to the electrode 12 the same manner as illustrated in FIG. 3. The lead 47 is, however, provided with an anchoring pad 48 which is formed integral with an insulation cover or jacket 49. The pad 48 has a generally flat bottom 50 and is of sufficient width and length to form an enlarged surface area for anchoring the lead with a suitable adhesive as previously described at a relatively short distance from the electrode 12.

In the process of attaching the electrodes 12 to the scalp 13 an area large enough for attaching the electrode in direct contact with the skin surface 38 is prepared, the electrode is placed against the skin surface and a suitable adhesive such as collodion is applied to form an adhesive layer surrounding the electrode and anchoring it in engagement with the skin surface. Care is taken to prevent filling the cavity 36 with collodion by blocking the opening 34 with suitable means. After anchoring of the electrode by application of the collodion to the electrode itself and also to the area around the insulating sleeve 42, the lead 14 is also anchored to the patient's scalp at a short distance from the electrode utilizing the anchoring sleeve 24 or the anchoring pad 48. The lead 14 may be anchored at the sleeve 24 or pad 48 by application of collodion 46 as illustrated in FIG. 3, and/or by anchoring the sleeve or pad with strips of adhesive tape 26. The section of lead 14 between the electrode 12 and the anchoring means may not require anchoring by adhesive or tape since the length of this section is relatively short and signals likely to be generated by its movement, however slight such movement is likely to be, will not be of sufficient magnitude to interfere with the signal being conducted from the electrode to the amplifier unit 16.

After the electrode 12 is suitably anchored including anchoring of the lead 14 at the preferred location, an electrically conductive gel of a type known for use with electroencephalographic electrodes may be injected into the cavity 36 to increase the conductive path between the surface of the skin and the electrode. The skin surface 38 may be prepared for maximizing the conductive engagement with the electrode 12 after application of the electrode to the skin and injection of the gel by inserting an instrument, such as blunt needle, through the opening 34 and rubbing the surface of the skin forming one boundary of the cavity 36.

Normally, all of the electrodes 12 are preferably attached to the patient's scalp or to such other places on the patient's body as may be required for recording signals generated by organs or muscles and the leads 14 then run to and connected to the amplifier unit 16. Since the length of the leads 14 is of little consequence the amplifier unit 16 may, in fact, be designed to be integral with the recording unit 22 and whereby the leads 14 may be conducted directly to the unit 22. However, the arrangement illustrated in FIG. 1 is believed to be less cumbersome as regards the routing of the several leads normally required for electroencephalography. When it is desired to remove the electrodes 12 and the respective associated leads the collodion adhesive may be dissolved by acetone to permit easy removal of the electrodes.

Those skilled in the art will appreciate that the embodiments of the improved electrode and lead assembly as well as the method of attachment of the electrodes described herein provides a substantial improvement in the art of ambulatory electroencephalography. The avoidance of mounting the preamplifier units directly adjacent to the electrodes is of substantial benefit to ambulatory patients, in particular. The delicate structure of the preamplifiers has also resulted in frequent breakage in prior art practice. However, this problem is substantially overcome with the arrangement of the present invention. The placement of several small electrodes and small leads on the patient's head without also requiring the mounting of amplifier circuitry directly adjacent to the electrodes is more attractive to the patient and provides a psychological benefit while the patient is required to carry out the electroencephalographic recording process.

Although the electrode 12 shown in conjunction with the lead and anchoring devices described herein is particularly useful other styles of electrodes may also be used in conjunction with the lead and anchoring means as well as the method of the present invention. The arrangement of anchoring the leads 14 at a point spaced from the electrode also minimizes the chance of unwanted removal of the electrode should the patient accidentally snag or jerk one of the leads 14 while wearing the system illustrated in FIG. 1.

Those skilled in the art of electroencephalography techniques and apparatus will appreciate the advantages of the invention described herein and will also recognize that various substitutions and modifications may be made to the specific embodiment shown and described without departing from the scope and spirit of the invention as recited in the appended claims.

What I claim is:

1. An electrode assembly for use in making electroencephalographic records and the like, said electrode assembly including:

a circular disk type electrode member including a flange portion adapted to be placed in electrically conductive relationship with a patient's body, said electrode member being adapted to be held substantially stationary at a predetermined point on said patient's body;

a flexible electrical conductor having a first end electrically connected to said electrode member and a second end adapted to be connected to a signal amplifier disposed remote from said electrode member;

a tubular sleeve secured to said conductor at a point spaced about one inch from said electrode member and providing an enlarged surface area for anchoring said conductor to the skin surface of said patient's body with adhesive means to minimize electrical interference induced by movement of said conductor between said electrode member and said amplifier, said conductor including a flexible insulation cover and said insulation cover being of a thickness such that at least a portion of said conductor between said tubular sleeve and said electrode member is suspended out of contact with said patient's body; and a connector member at said second end of said conductor for electrically connecting said electrode assembly to said amplifier.

2. An electrode assembly for use in making electroencephalographic recordings and the like, said electrode assembly including:
- a circular disk type electrode member including a flange portion adapted to be placed in electrically conductive relationship with a patient's body, said electrode member being adapted to be held substantially stationary at a predetermined point on said patient's body:
- a flexible electrical conductor having a first end electrically connected to said electrode member and a second end adapted to be connected to a signal amplifier disposed remote from said electrode member;
- said conductor including an insulation cover having an enlarged integrally formed pad portion disposed at a point spaced about one inch from said electrode member and providing an enlarged surface area for anchoring said conductor to the skin surface of said patient's body with adhesive means to minimize electrical interference induced by movement of said conductor between said electrode member and said amplifier, said insulation cover of the portion of said conductor between said pad portion and said electrode member being of a thickness such that said conductor between said pad portion and said electrode member is suspended out of contact with said patient's body; and
- a connector member at said second end of said conductor for electrically connecting said electrode assembly to said amplifier.

* * * * *